(12) United States Patent
Hedges et al.

(10) Patent No.: US 7,928,741 B2
(45) Date of Patent: *Apr. 19, 2011

(54) OIL MONITORING SYSTEM

(75) Inventors: Joe D. Hedges, Portola Valley, CA (US);
Paul J. Voelker, Fremont, CA (US)

(73) Assignee: Voelker Senors, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/426,956

(22) Filed: Apr. 20, 2009

(65) Prior Publication Data

US 2009/0201036 A1 Aug. 13, 2009

Related U.S. Application Data

(63) Continuation of application No. 11/676,738, filed on Feb. 20, 2007, now Pat. No. 7,521,945.

(60) Provisional application No. 60/774,749, filed on Feb. 17, 2006, provisional application No. 60/782,959, filed on Mar. 15, 2006.

(51) Int. Cl.
*G01R 27/26* (2006.01)
*G01N 33/26* (2006.01)

(52) U.S. Cl. ........................................ 324/698; 73/53.05

(58) Field of Classification Search .................. None
See application file for complete search history.

(56) References Cited

U.S. PATENT DOCUMENTS

| | | | |
|---|---|---|---|
| 2,862,859 A | 12/1958 | Grosskopf | |
| 3,182,255 A | 5/1965 | Hopkins et al. | |
| 3,386,859 A | 6/1968 | Biddick | |
| 3,410,780 A | 11/1968 | Holden | |
| 3,787,650 A | 1/1974 | Lewis | |
| 4,007,629 A | 2/1977 | Hochstein | |
| 4,345,202 A | 8/1982 | Nagy et al. | |
| 4,443,754 A | 4/1984 | King | |
| 4,606,222 A | 8/1986 | Stockmeyer | |
| 4,646,070 A | 2/1987 | Yasuhara et al. | |
| 4,679,007 A | 7/1987 | Reese et al. | |
| 4,733,556 A | 3/1988 | Meitzler et al. | |
| 4,764,258 A | 8/1988 | Kauffman | |

(Continued)

FOREIGN PATENT DOCUMENTS

EP 0442314 8/1991

(Continued)

OTHER PUBLICATIONS

Tim Sullivan, "Oil Sludge Bedevils VW," Lube Report, Aug. 31, 2004, http://www.lubereport.com/e_article000298526.cfm?x=b3t4ghV,bhb871W.

(Continued)

*Primary Examiner* — Jeff Natalini
(74) *Attorney, Agent, or Firm* — Carr & Ferrell LLP

(57) ABSTRACT

An embodiment of the present invention provides for a sensing element comprising a non-conductive housing with three chambers for detecting oil conductivity, additive depletion and oxidation, and water contamination, respectively. Through the monitoring of an array of oil sensors, an early warning of oil degradation due to oxidation is provided. The monitoring system further detects excess soot, water and other contaminants in the oil. The oil sensor array and related monitoring system decrease the likelihood of catastrophic engine failure through the early detection and warning of a decrease in oil quality thereby reducing vehicle owner outlays for servicing and disposal fees while further aiding in the satisfaction of environmental protection regulations.

14 Claims, 7 Drawing Sheets

U.S. PATENT DOCUMENTS

| | | | |
|---|---|---|---|
| 4,791,374 | A | 12/1988 | Yodice et al. |
| 4,857,829 | A | 8/1989 | Sagae et al. |
| 4,952,868 | A | 8/1990 | Scherer, III |
| 5,071,527 | A | 12/1991 | Kauffman |
| 5,089,780 | A | 2/1992 | Megerle |
| 5,141,717 | A | 8/1992 | McRae |
| 5,435,170 | A | 7/1995 | Voelker et al. |
| 5,777,210 | A | 7/1998 | Voelker et al. |
| 5,789,665 | A | 8/1998 | Voelker et al. |
| 6,286,363 | B1 | 9/2001 | Discenzo |
| 6,873,916 | B2 * | 3/2005 | Kolosov et al. ............ 702/25 |
| 7,521,945 | B2 * | 4/2009 | Hedges et al. ............ 324/698 |
| 2003/0147073 | A1 | 8/2003 | Abraham et al. |
| 2004/0036487 | A1 | 2/2004 | Heremans et al. |
| 2004/0178900 | A1 | 9/2004 | Berndorfer et al. |
| 2004/0212378 | A1 | 10/2004 | Sohl, III et al. |
| 2004/0257094 | A1 | 12/2004 | Halalay et al. |
| 2004/0263187 | A1 * | 12/2004 | Hayashi et al. ............ 324/698 |

FOREIGN PATENT DOCUMENTS

| | | |
|---|---|---|
| EP | 0584557 | 7/1992 |
| GB | 939049 | 10/1963 |

OTHER PUBLICATIONS

"Oil Advantage: In-line Oil Monitoring System," Voelker Sensors Inc., 2004.

"Assured Oil Performance at a Glance," Voelker Sensors Inc., 2004.

"Oil Advantage: Low Cost In-line Oil Monitoring System," Voelker Sensors Inc., 2006, VSI.

Elecia White, "Due for an Oil Change?" Putting Sensors to Work, Sensors, Apr. 2005, pp. 27-29.

Mike Allen, "Dirty Deeds Done Dirt Cheap," Car Clinic, Car Care, Popular Mechanics, Aug. 1993, p. 71.

R.T. Mookken et al., "Dependence of Oxidation Stability of Steam Turbine Oil on Base Oil Compositio ©," Journal of the Society of Tribologists and Lubrication Engineers, Dec. 3, 1996, pp. 19-24.

W.F. Bowman et al., "Application of Sealed Capsule Differential Scanning Calorimetry-Part II: Assessing the Performance of Antioxidants and Base Oils ©" Technical Paper, Lubrication Engineering, May 1999, pp. 22-29.

W.F. Bowman et al., "Application of Sealed Capsule Differential Scanning Calorimetry-Part I: Predicting the Remaining Useful Life of Industry-Used Turbine Oils ©," Journal of the Society of Tribologists and Lubrication Engineers, Aug. 18, 1998, pp. 19-24.

Jun Dong et al., "Rapid Determination of the Carboxylic Acid Contribution to the Total Acid Number of Lubricants by Fourier Transform Infrared Spectroscopy ©," Technical Paper, Journal of the Society of Tribologists and Lubrication Engineers, Aug. 30, 1999, pp. 12-20.

Han-Sheng Lee et al., "In-Situ Oil Condition Monitoring in Passenger Cars ©," Journal in Society of Tribologists and Lubrication Engineers, 1993, vol. 50, No. 8, pp. 605-611.

R.E. Kauffman, "Rapid, Portable Voltammetry Techniques for Performing Antioxidant, Total Acid Number (TAN) and Total Base Number (TBN) Measurements ©," Technical Papers, Journal of the Society Tribologists and Lubrication Engineers, Jan. 1998, pp. 39-46.

Atsushi Sato et al., "Electrical Conductivity Method for Evaluation of Oxidative Degradation of Oil Lubricants ©," Journal of the Society of Tribologists and Lubrication Engineers, Jul. 1992, vol. 48, No. 7, pp. 539-544.

* cited by examiner

Relative Low Conductivity

Relative High Conductivity

OIL MONITORING SYSTEM

CROSS-REFERENCE TO RELATED APPLICATIONS

The present application is a continuation and claims the priority benefit of U.S. patent application Ser. No. 11/676,738, now U.S. Pat. No. 7,521,945, filed Feb. 20, 2007, which claims the priority benefit of U.S. provisional patent application No. 60/774,749 filed Feb. 17, 2006 and U.S. provisional patent application No. 60/782,959 filed Mar. 15, 2006. The disclosure of the aforementioned applications is incorporated herein by reference.

The present application is related to U.S. Pat. No. 5,435,170, entitled "Method and Apparatus for Fluid Quality Sensing"; U.S. Pat. No. 5,777,210, entitled "Oil Quality Sensor Measuring Bead Volume"; and U.S. Pat. No. 5,789,665 entitled "Oil Quality Sensor for Use in a Motor Oil." The disclosure of these commonly owned patents is incorporated herein by reference.

BACKGROUND OF THE INVENTION

1. Field of the Invention

The present invention relates generally to measurement and testing for liquid analysis. More specifically, the present invention relates to the analysis of natural and synthetic oils for the purpose of detecting oil degradation and, further, for detecting the presence of contaminates such as soot, fuel and water. Oxidation and the presence of contaminates may be interpreted as an indication of the quality of the oil or any other non-polar liquid.

2. Description of the Related Art

Determining oil quality is a complex issue. Four methods of measuring and testing lubricating oil quality are generally accepted in the art: infrared spectroscopy, pH measurement, viscosity, and prediction of degradation.

Infrared spectroscopy utilizes a portion of the infrared region of the electromagnetic spectrum for analyzing organic compounds. For example, photon energies associated with the wavelength range of 2,500 to 16,000 nm, which corresponds to a frequency of approximately $1.9 \times 10^{13}$ to $1.2 \times 10^{14}$ Hz, are not large enough to excite electrons. These photon energies may, however, induce vibrational excitation of covalently bonded atoms and groups. As molecules experience a variety of vibrational motions characteristic of their component atoms, virtually all organic compounds will absorb infrared radiation that corresponds (in energy) to these vibrations. Infrared spectrometers obtain absorption spectra of compounds that are a unique reflection of their molecular structure.

While infrared spectroscopy offers the advantage of determining a number of oil qualities—including and in addition to lubricity—this methodology requires the removal of an oil sample from a source (e.g., removing oil from the motor of an automobile) and placing the oil sample in an infrared spectrometer. In addition to being expensive, this methodology is not conducive to 'on-the-fly' testing. Absent infrared spectrometers being introduced as standard equipment in automobiles and other machines that utilize natural and synthetic oils, infrared spectroscopy cannot be utilized to provide instantaneous indications of oil quality and/or that oil needs to be changed.

The second method of measuring and testing lubricating oil quality—pH measurement—is a logarithmic measurement of the number of moles of hydrogen ions per liter of solution. Thus, pH measures the hydrogen ion concentration in a liquid solution such as natural and synthetic oils. Low pH values (e.g., 0) indicate acidity and high pH values (e.g., 14) indicate causticity. Continual process monitoring and control of pH requires the use a specially prepared electrode (i.e., the measurement electrode). This specially prepared measurement electrode is designed to allow hydrogen ions in the solution to migrate through a selective barrier thereby producing a measurable potential difference proportional to the solution's pH.

While the pH of oil provides an indication of changes in acidity or causticity with regard to the presence (or absence) of certain acids, pH does not measure oil lubricating quality. Further, pH measurements do not determine if the oil has degraded due to foreign particles and contaminants such as water or metal particulate. Additionally, pH measurements can be skewed by the presence of volatile acids that evaporate over time at certain operating temperatures. The presence and/or subsequent evaporation of those acids can provide a false and/or inconsistent pH reading that is not relative to the actual quality of the oil being measured. A pH sensor apparatus, too, is expensive and not particularly suited for the environment of the oil pan of an internal combustion engine.

The third measurement methodology—prediction of degradation—is simple to a fault. Based on the knowledge that oil maintains a particular quality over a period of time, the mileage traversed since a previous oil change in a vehicle can be utilized to inform the owner of the vehicle that it is time to replace the oil. The timing of the indicia of replacement (e.g., the activation of a dashboard warning light) is based on the prediction of degradation and that the oil is no longer providing particular performance guarantees as governed by the quality of the oil.

This methodology, however, does not take into account the various qualities or quantities of oil that may be used in a particular vehicle. This methodology further fails to account for the particularities of the engine operating environment (e.g., engine wear independent of the oil quality) in addition actual driving conditions (e.g., city or highway, summer or winter, and so forth). This methodology, in addition to its overall inaccuracy, provides no qualitative or quantitative information regarding oil condition in that the indicia of the need for oil replacement is purely binary (i.e., time-to-change or not time-to-change).

A fourth technique measures the viscosity of the oil. As a result of the oxidation process, oil becomes thicker. A thickening of the oil can be an indication of the extent of oil breakdown.

While viscosity can provide an indication of oil wear, viscosity is dependent on the temperature and the particular viscosity improvement package added to the oil. For a viscosity measurement to provide an accurate measurement of oil quality, the temperature and type of viscosity improvement package must be known. The presence of contaminates will further increase or decrease the viscosity of a particular oil sample thereby hampering measurement.

As previously noted, base engine oils are non-polar and provide near-zero conductivity when clean. As the oil wears, the oil slowly begins to oxidize and exponentially increase in polarity as is shown in FIG. 1. FIG. 1 illustrates oil that, initially, is clean and non-polar. In the presence of $O_2$ and heat, the oil begins to degrade. This application of $O_2$ and heat would occur through, for example, the normal and ongoing use of the oil in an automobile.

This partially degraded oil, as also shown in FIG. 1, begins to take on polar characteristics. Through the continued application of $O_2$ and heat, the oil becomes even more degraded and takes on even grater polar characteristics as further shown in FIG. 1. Increased polarity causes the oil to change is dielectric constant, which in turn leads to increased capacitance.

Most fully formulated oils incorporate deposit control additives, anti-wear and extreme pressure additives, corrosion inhibitors, and antioxidants. These protective additives generally consist of a polar salt head and a nonpolar hydrocarbon tail to trap harmful byproducts of oil wear. Depending on the exact concentration of various additives, the oil's dielectric constant and conductivity will vary according to the manufacturer, batch, and base type.

Clean and fully formulated oil typically has a higher starting capacitance than that of worn base oil. Because of this higher capacitance, electrical measurement of clean oil actually measures the additive package and not the properties of the base oil. Oil deterioration also results in a decrease of additives. As the dielectric constant of the oil becomes greater than that of the additives in the oil, useful direct oil analysis becomes difficult if not impossible.

While a variety of means are known in the art to measure oil pressure, there is a general lack of means to accurately and effectively measure oil quality. Those sensors that do exist often encounter the aforementioned problem of differentiating increases in oil dielectric constant versus presence and quality of oil additives. Measurement of oil quality is important in that the oil in a vehicle or other mechanical device needs to be changed when the oil loses its lubricity or becomes populated with contaminates.

There is a general need in the art for means to measure oil quality notwithstanding changes in oil dielectric constants. There is a further need in the art for monitoring an array of sensors in the oil thereby providing an early warning of degradation due to oxidation and detecting excess soot and water.

SUMMARY OF THE INVENTION

The present invention provides for differential measurement of specific conditions of contaminates in oil. Measurement of these conditions may provide indicia of oil quality. While the breakdown of the base stock alone is, in some instances, a key indicator of oil wear, contamination by soot, fuel, and/or water may also be important parameters with respect to determining oil quality. The presently disclosed differential measurement technique employs sensing elements that may measure substantially identical properties with a single exception thereby allowing for a specific attribute to be measured. Embodiments of the present invention may be implemented in the context of the polystyrene bead matrices disclosed in U.S. Pat. Nos. 5,435,170; 5,777, 210; and 5,789,665. The disclosure of the aforementioned patents has been previously incorporated herein by reference.

In one embodiment, an oil quality monitoring system is comprised of a sensing element configured to generate oil measurement data associated with oil quality of a monitored oil sample, the sensing element comprising a housing and a plurality of chambers within the housing. A monitoring device is coupled to the sensing element. The monitoring device includes an application specific integrated circuit configured to differentially analyze the oil measurement data generated by the sensing element. The device may be further configured to display an indicia of oil quality of the monitored oil sample in a user interface based on the differential analysis of the oil measurement data.

In a further embodiment, an oil quality monitoring system is provided that includes an array of sensing elements configured to generate oil measurement data associated with oil quality of a monitored oil sample. Each of the sensing elements in the array of sensing elements includes a housing and a plurality of chambers within the housing. A monitoring device coupled to the array of sensing elements may provide for differential analysis of the oil measurement data generated by the array of sensing elements. The monitoring device may further display an indicia of oil quality of the monitored oil sample in a user interface based on the differential analysis of the oil measurement data.

DETAILED DESCRIPTION

Figure 1:
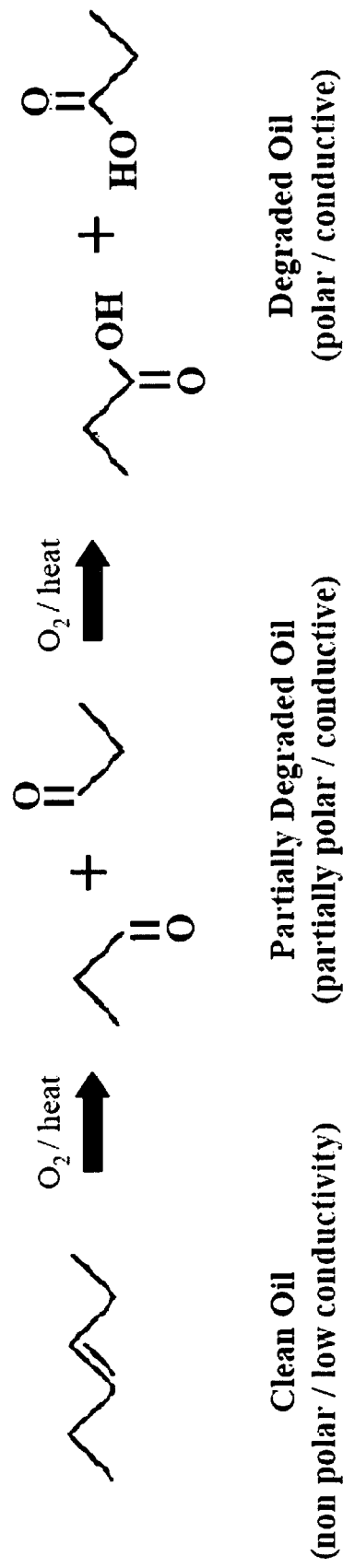
FIG. 1 illustrates the wear of oil due to oxidation and heat whereby the oil becomes more polar as is known in the prior art.
Figure 2:
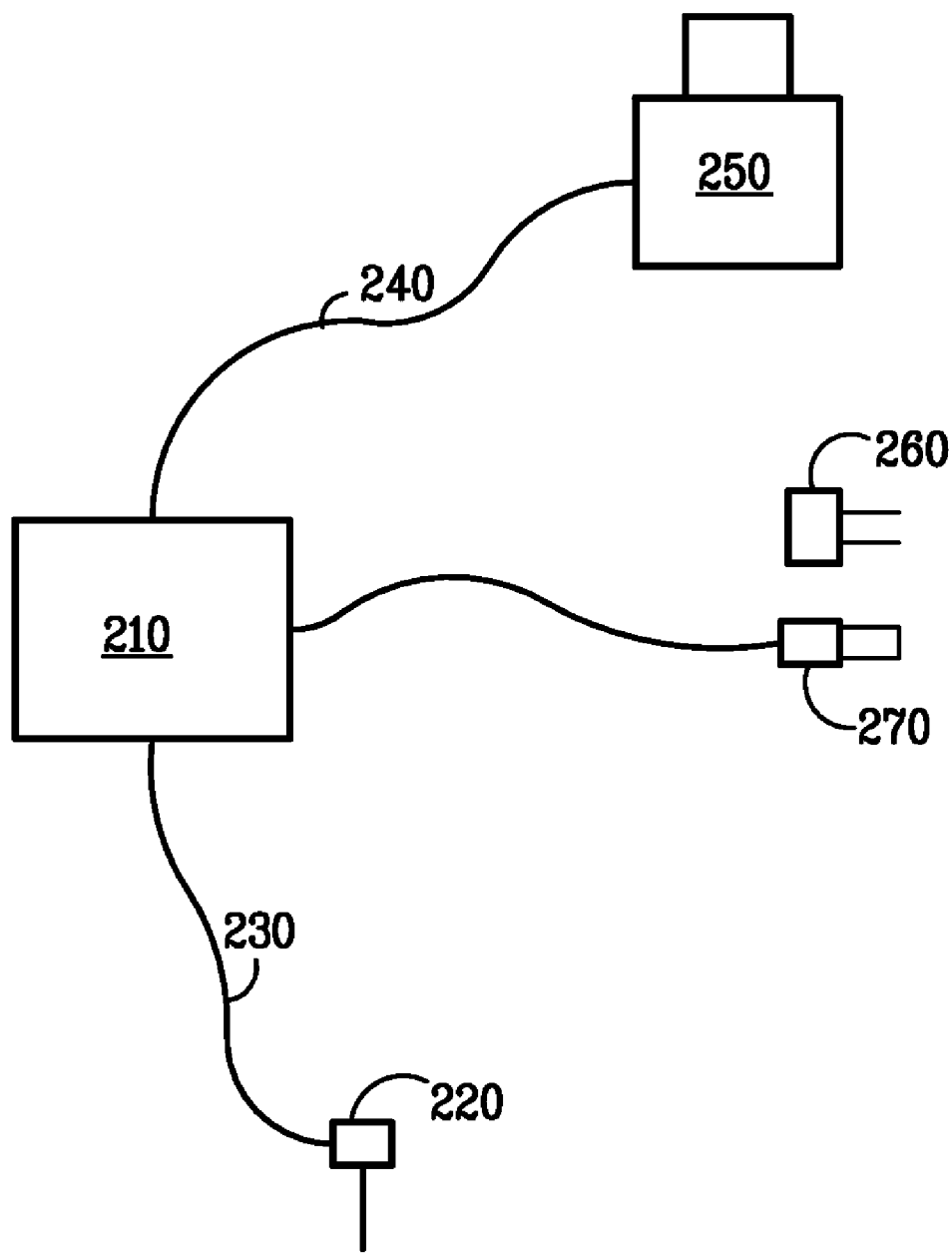
FIG. 2 illustrates an exemplary real-time oil monitoring system as may be implemented in accordance with an embodiment of the present invention.

FIG. 2 illustrates an exemplary real-time oil monitoring system 200 as may be implemented in accordance with an embodiment of the present invention. An embodiment of the oil monitoring system 200 may comprise a monitoring device 210 for receiving and analyzing data generated by a sensing element 220, which is in contact with the oil or other fluid under observation.

Data generated by the sensing element 220 may be communicated to the monitoring device 210 via a sensor signal cable 230. Sensor signal cable 230, in one embodiment of the present invention, is an RS-232 compliant serial cable wherein one end of the cable is configured to exchange data with the monitoring device 210 and the opposite end of the cable is configured to interface with sensing element 220 as is discussed in greater detail in FIG. 3. Other data cables are within the scope of the present invention subject to proper configuration to allow for interface with the sensing element 220 and monitoring device 210.

Monitoring device 210 may be further communicatively coupled to an external computing device 250 such as a laptop computer, a PDA or other mobile computing device that may be specially configured for use with the oil sensing element 220 and monitoring device 210. While mobility of the external computing device 250 may be preferred in some environment (e.g., a garage), it is within the scope of the present invention for the external computing device 250 to be a less-portable computing device such as a dedicated workstation or desktop computer. Data may be exchanged between the monitoring device 210 and external computing device 250 through, for example, an external data cable 240 or a wireless network connection.

External data cable 240 may comply with any number of data transmission standards including Universal Serial Bus (USB) and IEEE 1394 in addition to being a parallel or serial data cable. In some embodiments of the present invention, monitoring device 210 may be configured for the introduction of, for example, a PCMCIA wireless card or other wireless network adapter. In such an embodiment, the monitoring device 210 may communicate data gathered from the sensing element 220 as well as data analyzed by the monitoring device 210 wirelessly using, for example, the 802.11x wireless data standard to external computing device 250 such that external data cable 240 is no longer necessary.

A wireless configuration of this nature would allow increased mobility of the monitoring device 210 while still allowing, for example, for the storage of oil data in a centralized repository such as the aforementioned external computing device 250. Storage of oil measurement data and analyses of that data may be useful in determining if a particular vehicle or combustion engine might be suffering from engine damage or some other defect in that the particular vehicle or engine prematurely degrades oil. Such information may be reflected by a series of oil analyses conducted over time. These analyses may be stored, further analyzed, and graphically illustrated in a report or some other organized information presentation generated by external computing device 250. It should be noted that the presence of an external computing device 250 is not required for the operation of the monitoring device 210 in conjunction with sensing element 220.

The monitoring device 210, in one embodiment of the present invention, receives and displays data indicative of the status of the oil or another fluid under observation and analysis. The interface of monitoring device 210 is discussed in more detail in FIG. 7 below.

Monitoring device 210 and certain devices coupled to device 210 may be powered by a variety of electrical power sources. In one embodiment of the present invention, monitoring device 210 may be electrically coupled to an AC transformer 260. In another embodiment of the present invention, monitoring device 210 may be electrically coupled to a DC transformer such as a cigarette lighter adaptor whereby the system 200 may be used 'on-the-road' through use of an automobile's cigarette lighter power outlet. Monitoring device 210 may further be powered by a replaceable or rechargeable battery pack (not shown).

In an embodiment of the present invention, the monitoring device 210 may also comprise a thermistor configured to be used by a microprocessor in the device 210 to compensate sensor readings for thermal variations. For example, in one embodiment of the present invention, the system 200 may only operate at engine operating temperatures in excess of, for example, 70° C. as the conductivity of certain oils may be completely masked by the additives below that temperature. Additionally, because oil is formulated to work at automotive operating temperatures, the oil may not properly lubricate at lower temperatures thereby distorting data gathered by the sensing element 220.

Figure 3:
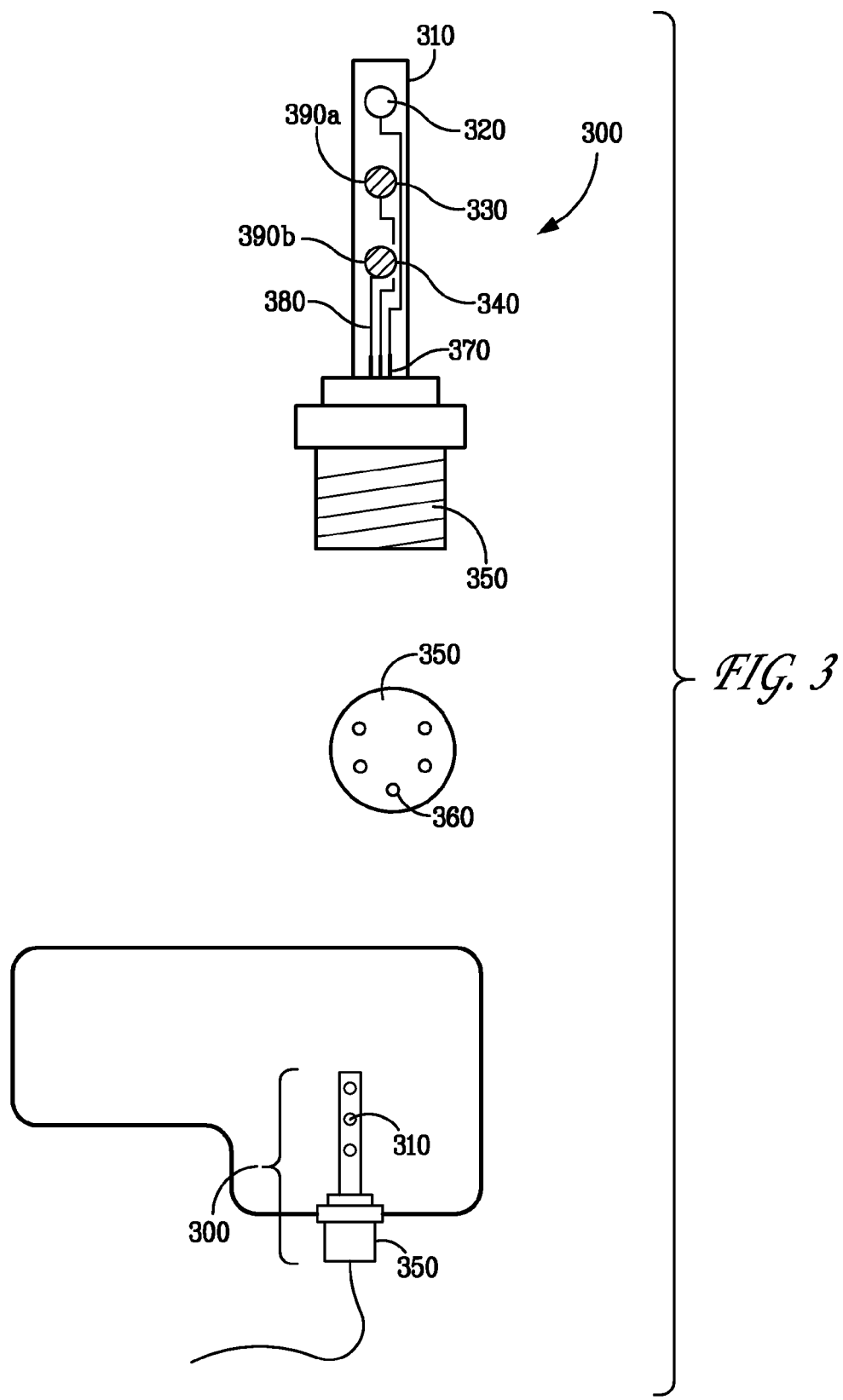
FIG. 3 illustrates an exemplary embodiment of a sensing element as may be used in the present invention in addition to an inset reflecting the installation of the sensing element in an oil pan.

FIG. 3 illustrates an exemplary embodiment of a sensing element 300 as may be used in the present invention. The inset of FIG. 3 reflects the sensing element 300 having been installed in an oil pan. Sensing element 300 comprises an electrically nonconductive housing 310 with three chambers (320, 330, and 340). Examples of non-conductive materials for constructing the housing 310 include but are not limited to ceramic, glass, plastic, woven fiberglass, and paper impregnated with phenolic resin (e.g., Pertinax).

In some embodiments of the present invention, the housing 310 may be constructed of an electrically non-conductive material. In other embodiments, the housing 310 may instead be constructed of one or more materials (which may or may not be electrically non-conductive) and subsequently coated with an electrically non-conductive material such as a non-conductive resin cured with ultraviolet light and/or heat. In addition to non-conductive resins, other suitable coating materials include but are not limited to tape, paints and hot melt adhesives.

Housing 310 may be mounted in a conventional drain plug 350 such that the sensing element 300 may be installed in a conventional oil pan of an internal combustion engine. Mounting of the housing 310 may occur utilizing various industrial glues, sealants, adhesives or other means so long as such mounting means do not interfere with the sensing element 300's ability to communicate with cable connector pins 360 as discussed in greater detail below.

By mounting the housing 310 of the sensing element 300 in a conventional drain plug 350, an embodiment of the present invention may be installed in older automobiles or equipment utilizing a combustion engines without the need for extensive retrofitting as the drain plug 350 may simply be threaded into the oil pan's drain hole as would occur when changing the oil of a car. An embodiment of drain plug 350 used for mounting the housing 310 of the sensing element 300 may utilize ½"× 20 threading such than an exemplary sensing element 300 measuring approximately 2.8" in length occupies an internal depth of approximately 1.8".

The particular mechanical interface (e.g., shape and threading specifications) of the aforementioned drain plug 350 are exemplary as are the particular dimensions of the sensing element 300. The drain plug 350 may utilize any variety of physical configurations (e.g., hex nut) and threading arrangements and may further be specially manufactured for particular combustion engine/oil pan/engine environments. The sensing element 300 (as a part of or independently of the drain plug 350) may also utilize any variety of O-rings, washers, and/or protective housings in order to properly protect the sensing element 300 and to otherwise ensure that housing 310 is properly secured within the drain plug 350.

Figure 4:
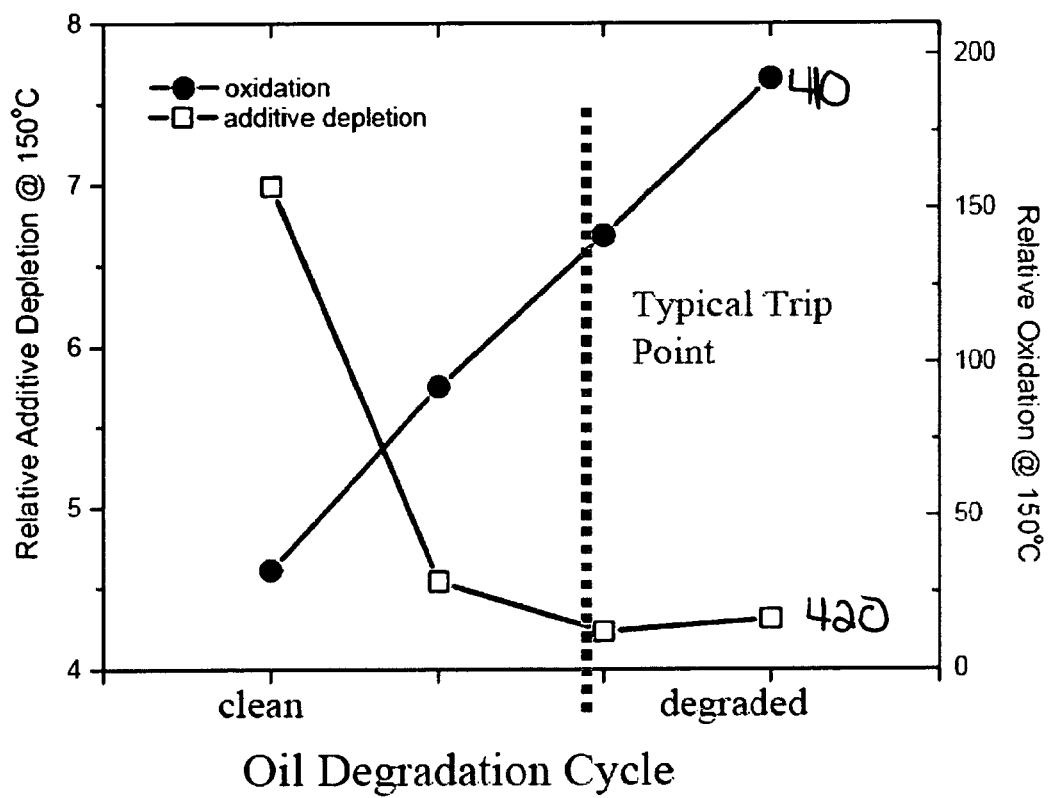
FIG. 4 is an exemplary illustration of the oil degradation cycle.

One of the three chambers of sensing element 300 (e.g., chamber 320) is open. Chamber 320 detects the conductivity of the oil directly. With regard to chamber 320, conductivity is dominated by the ionic characteristics of oil additives (oxidation 410) as is shown in the exemplary oil degradation cycle depicted in FIG. 4. In the oil degradation cycle of FIG. 4, as additives are depleted the additives become less polar; as the base oil itself deteriorates, the base oil becomes more polar.

Returning to FIG. 3, the remaining two chambers (chambers 330 and 340) are covered by a conductive mesh screen (390a and 390b). Chamber 330 comprises (houses) a matrix of insoluble polymeric beads (not shown). Chamber 340 comprises a single bead (not shown). The conductive mesh screen (390a and 390b) may be constructed of stainless steel cloth.

Figure 5A:
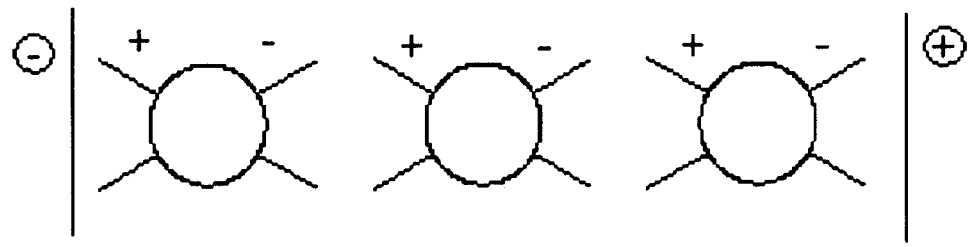
FIG. 5A is an exemplary illustration of polymeric bead interaction in a non-polar oil solution representative of relatively low conductivity in an exemplary embodiment of the present invention.
Figure 5B:
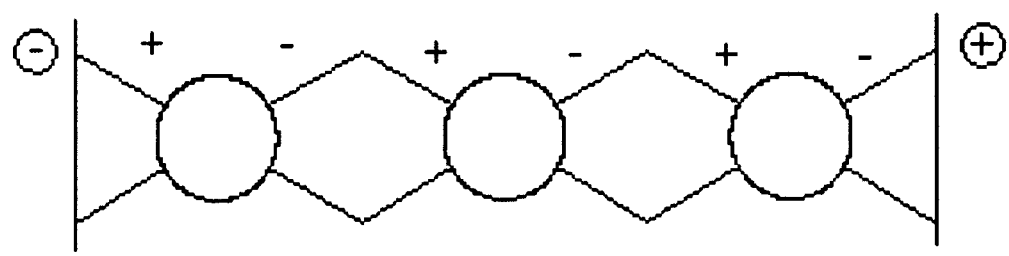
FIG. 5B is an exemplary illustration of polymeric bead interaction in a polar oil solution representative of relatively high conductivity in an exemplary embodiment of the present invention.

In a non-polar solution with relatively low conductivity, the beads in chamber 330 remain separate from one another as is shown in FIG. 5A. It should be noted that in FIG. 5A as well as FIG. 5B—for the sake of simplified illustration—only a single monolayer of the charged bead matrix is shown. The fact that only a single monolayer is illustrated should not be interpreted as otherwise limiting the present disclosure. As the oil's polarity increases, however, the conductivity across the matrix increases and the ionic component of each group of beads relaxes and begins electrically interacting with an adjacent group in the presence of voltage potential. FIG. 5B illustrates the same whereby the beads form a bridge on the conductive mesh 390*a* of the chamber 330. The change in the bead matrix as illustrated in FIGS. 5A and 5B indicates both additive depletion and oxidation and is represented graphically by line 420 (additive depletion) in FIG. 4.

The sensing element 300 generates a sensor reading reflective of oxidation based on a differential measurement of a matrix of insoluble polymeric beads and the oil being analyzed. Sensing element 300 further generates a sensor reading reflective of the presence of soot and similar contaminants based on a differential measurement of oil inside a filter and the oil being analyzed. Sensing element 300 further generates a sensor reading reflective of the presence of fuel, water or similar contaminants based on a differential measurement of a matrix of insoluble polymeric beads and the contaminated oil being analyzed. The sensing element 300 may measure oil quality through the use of any one of a number of different electrical forms including alternating current (AC), direct current (DC), a combination of AC/DC, in addition to mechanical forms such as crystal resonance. By utilizing sensor readings from the three chambers of the sensor array, an accurate measurement of oxidation, additive depletion, and contamination is provided, which is more accurate reflection of oil quality Data readings from open chamber 320 are subtracted from data readings obtained from the bead matrix in chamber 330. This subtraction of data may take place in a differential analysis software module (not shown) in monitoring unit 210 under the control of a microprocessor (also not shown). Various other hardware and software elements may be present in monitoring unit 210 to allow for the receipt, processing, analysis, storage, and/or exchange of data. For example, one embodiment of the present invention may utilize an application specific integrated circuit (ASIC) for undertaking the differential analysis otherwise performed by the aforementioned software module. Through the subtraction of the open chamber 320 data, effects of additives are removed from the analysis and only oxidation is measured. In this regard, no calibration of the system 200 is required and any differences in various oil formulations are negligible with regard to a determination of oxidation in the oil under analysis.

This differential measurement technique may be used to determine the polarity of oil where one chamber measures multiple properties of the oil and a second chamber measures the same properties with the exception that it does not measure the polarity of the oil. Taking a differential measurement between the two chambers allows for a determination of the polar condition of the oil. Specifically, if an electrical measurement of the oil is made and a second electrical measurement is made of an ionic polystyrene matrix where the electrical signal includes components from both the oil and the polystyrene matrix then the difference between the signals shows the polarity of the oil.

Chamber 330 may determine soot contamination in an oil sample wherein the sensing element 300 has been disposed. Soot particulates consist primarily of carbon and tend to bind to one another and to the actual engine. If soot is allowed to aggregate unfettered, the soot particulates can actually begin to score the engine bearings. Soot measurement is based on a percentage of the amount of soot freely available in the oil and is commonly referred to as the saturated relative contamination. A given amount of free soot can, in some instances, constitute 1% to 2% contamination for base oil without additives or greater than 7% for fully formulated oils.

When a soot dispersant additive begins to fail, the soot begins to adhere to the surface of the aforementioned polymeric beads and form a bridge across the chamber 330. When such a bridge occurs, sensor readings at chamber 330 change dramatically and continue to increase as more layers of carbon soot accumulate. Conductivity caused by soot is considerably greater than that due to oil and additive polarity and is measurable by the present sensing element 300 in addition to capable of being differentiated versus worn oil.

Soot contamination may be determined using a differential measurement. By using two chambers—one that measures the properties of the oil and the other that measures the properties of the oil after it has passed thru a fine filter that keeps soot or any other contaminates away from the sensor—soot contamination can be measured. Specifically, soot that is not chemically capped is electrically conductive. Taking the differential measurement of two chambers where one measures all the electrical characteristics of the oil and the other is precluded from measuring the effect of the soot (or any other particle) in the oil by a 0.2 micron filter allows for a determination of soot contamination. This technique is not limited to an electrical measurement; it could also be used in an optical measurement.

The third chamber—chamber 340—may detect water contamination in the oil or fluid under investigation. Water that enters the engine and boils as a result of engine temperature can cause the engine oil to turn into a sludge-like substance. This sludge-substance not only fails to properly lubricate various engine components but can also rust an engine from the inside-out.

A determination of water contamination in oil may be made using a differential measurement technique. By immersing two sensor chambers into the oil—one that measures multiple properties of the oil and the other measures multiple properties less the property associated with water contamination—and using a differential technique, the water contamination may be independently measured. Specifically, if an electrical measurement of polystyrene matrix is made where the matrix is relatively insensitive to water contamination and the signal is compared to a measurement of the polystyrene matrix that is highly sensitive to water absorption, the difference between the measurements will allow the water contamination to be measured.

The measurement may be made electrically or mechanically by looking at the change in electrical characteristics of the beads or by looking at the change in physical characteristics of the beads. Using a highly cross-linked polystyrene matrix will limit both the mechanical and electrical changes to the bead matrix. Using a loosely cross-linked polystyrene bead matrix will allow for large changes in the electrical and mechanical properties of the beads. The change is proportional to the quantity of water contamination.

Conventional methodologies report water in oil as a percentage of total volume. Different blends of oil, however, can consume varying amounts of water as a result of oil additives binding with water molecules. As such, an absolute measure of water it not necessarily helpful or informative. An embodiment of the present invention reports water content as a percent saturated relative humidity (SRH) of the oil. An SRH of, for example, 100% where the oil cannot absorb any more water without its dropping out of solution as emulsified or free water is same for all oils at a given temperature.

As noted above, a single polystyrene bead in chamber 340 measures water contamination corresponding to 2% SRH. The diameter of the bead is slightly less than the thickness of the sensor housing/sensor board 310. The bead is extremely hydrophilic and attracts water, swells and physically contacts the conductive mesh screen 390b of the chamber 340. The resulting increase in conductivity is detected as shown in FIGS. 6A and 6B.

Figure 6A:
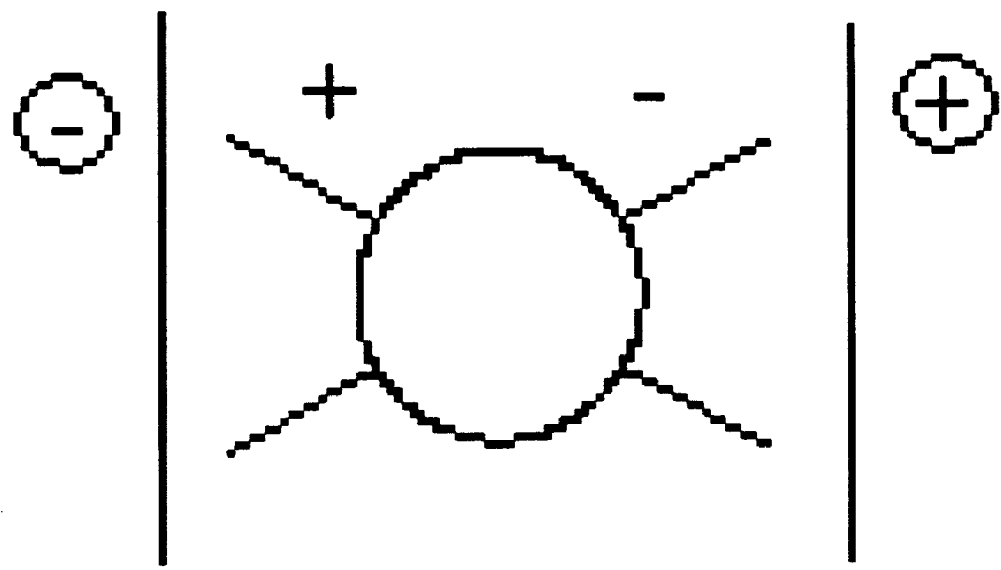
FIG. 6A illustrates a single hydrophilic, polystyrene bead in an environment without 'free' water and reflecting relatively low conductivity.
Figure 6B:
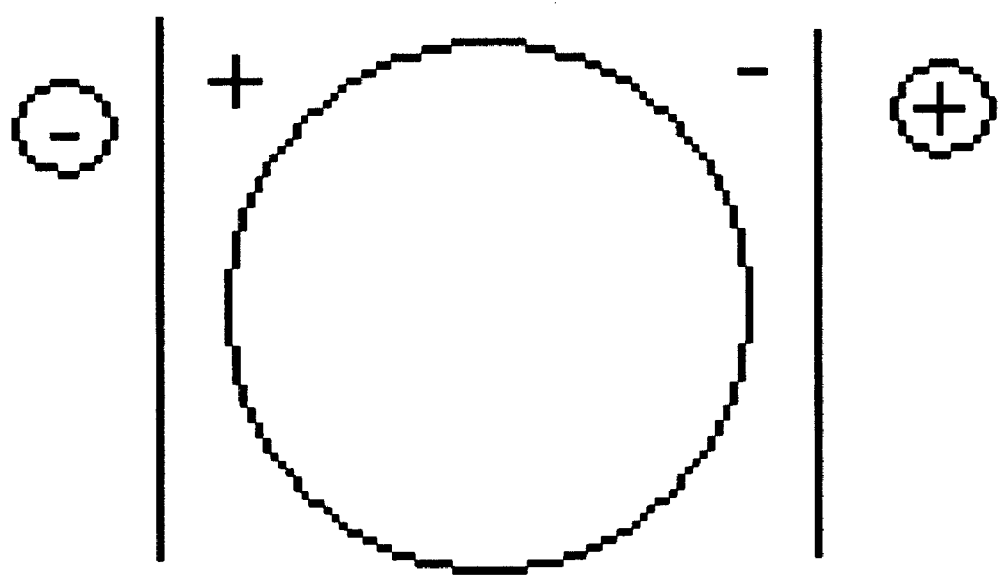
FIG. 6B illustrates a single hydrophilic, polystyrene bead in an environment with 'free' water and reflecting relatively high conductivity.

FIG. 6A illustrates a single hydrophilic, polystyrene bead in an environment without 'free' water and reflecting relatively low conductivity. FIG. 6B, however, illustrates the same single hydrophilic, polystyrene bead in an environment with 'free' water (i.e., water contamination) whereby the bead swells through its attracting of the 'free' water and comes into contact with camber 340's conductive mesh 390b thus reflecting relatively high conductivity.

The polystyrene beads of the present invention may be impregnated with charged groups. In one exemplary embodiment, sodium and sulfite may be utilized as the cation and anion, respectively. Salts of polyatomic anions such as phosphates and carboxylates may also be utilized as cation exchange groups. Additionally, anionic exchange groups may comprise salts of N-alkylated amines. The beads may be cross linked with 8% divinylbenzene and further comprise a titer or exchange capacity of 1.7 meq/ml. The beads, further, may be of 1.180 to 38 μm in diameter; 500 mg of which being sufficient in the present invention although lesser (and greater) amounts are possible in the practice of the present invention (e.g., 20 mg).

The beads utilized in various embodiments of the present invention may be pre-treated or 'prepared' in order to created a polar environment that allows for more accurate measurement of conditions in a non-polar environment such as uncontaminated oil solutions.

Such a process may include washing the beads with 1N sodium hydroxide for approximately 15 to 30 minutes at room temperature; the excess sodium hydroxide is washed off in a methanol bath. The beads are further soaked in methanol to remove any excess water and then air dried to remove any remaining methanol. The beads are subsequently soaked in glycerol for approximately 24 hours and then heated to approximately 140° C. for approximately two hours to ensure proper penetration of the glycerol. At this point, the beads are fully swollen.

The beads are then placed in a non-polar fluid (e.g., clean oil) and again heated to 120° C. to remove excess ethylene glycol and to further 'shrink' the beads to a 'clean oil' state. The beads are then loaded into the various chambers (e.g., 330 and 340) of the sensing element 300. The beads are typically loaded into the various chambers (e.g., 330 and 340) of the sensing element 300 under slight to moderate pressure such that the beads are in close proximity to one another. In an alternative embodiment, the beads may be further soaked in glycerol to cause slight expansion of the beads and otherwise obtain bead-to-bead proximity.

Data readings from sensing element 300 are communicated to the monitoring device 210 of system 200 through any number of wire tracings 380 on/in the non-conductive housing 310 of element 300. The conductive pathways of the wire tracings 380 are, in some embodiments, etched from copper sheets laminated onto the non-conductive housing 310. In other embodiments, traces may be added through electroplating. Various other methodologies for creating the conductive wire tracings 380 on the non-conductive housing 310 including but not limited to silk screen printing, photoengraving, and milling. In some embodiments of the present invention, a series of layers of substrates may make up the non-conductive housing 310 and a series of blind and/or buried vias (not shown) may be used instead of (or in addition to) surface mount methodologies.

These conductive pathways are coupled (e.g., through soldering) to chambers 310-340 in addition to output connectors 370, which (in one embodiment of the present invention) extend outward from the drain plug 350 and toward the various elements on the face of the non-conductive housing 310 of sensing element 300. Output connectors 370 serve to couple the wire tracings 380 on the face of the non-conductive housing 310 to cable connector pins 360 which extend outward from the drain plug 350 (and away from the non-conductive housing 310) such that the connector pins 360 may be connected to sensor signal cable 230 for data exchanges with monitoring device 210. In this way, data generated at the various chambers 310-340 may be communicated through wire tracings 380 to the output connectors 370, which connect to cable connector pins 360.

In some embodiments, output connectors 370 and cable connector pins 360 may be the same uninterrupted element whereby the pins 360 extend through the drain plug housing 350 and toward the non-conductive housing 310 where one end of the connectors are soldered to the wire tracings 380. In additional embodiments of the present invention, that portion of the drain plug 350 most distant from the oil pan or chamber into which the non-conductive housing 310 is inserted may have a concave design such that the cable connector pins 360 are partially or entirely housed within the concave area and protected from damage through exposure to the elements that might corrode the face of the pins 360 or deform the shape of the pins 360 (e.g., bending) through impact or other applied forces.

Figure 7:
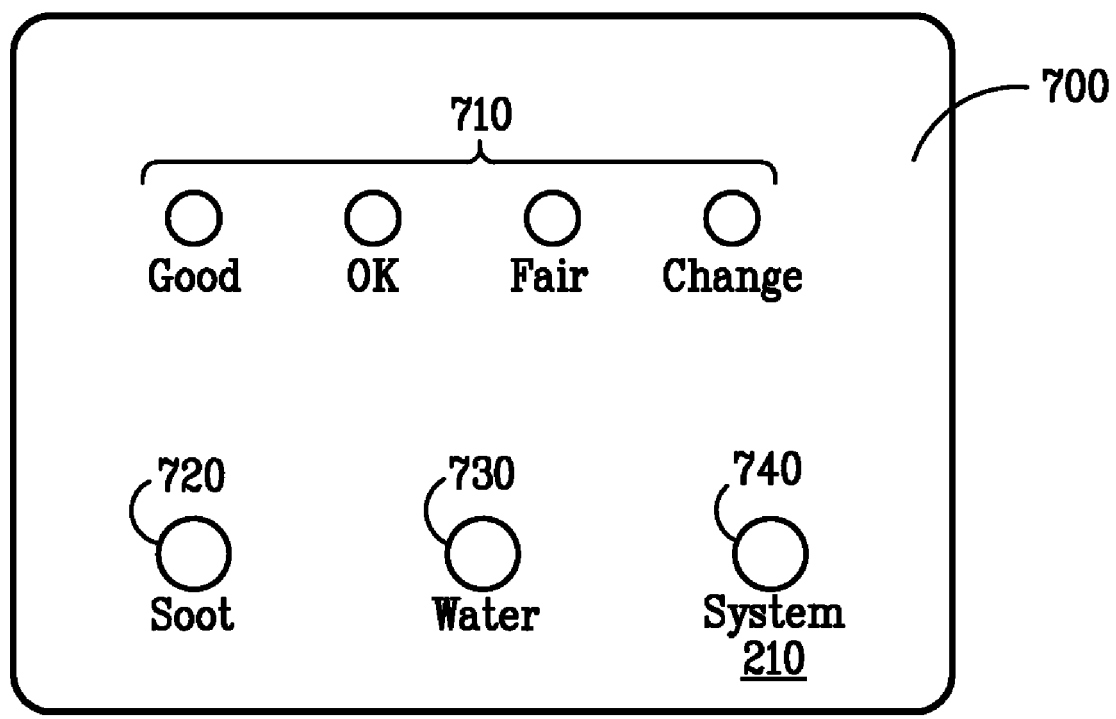
FIG. 7 illustrates an exemplary interface as may be used with a monitoring device of an exemplary embodiment of the presently disclosed oil monitoring system.

FIG. 7 illustrates an exemplary interface 700 as may be used with a monitoring device 210 of an exemplary embodiment of the presently disclosed oil monitoring system 200. After the aforementioned differential analysis software module of the monitoring device 210 has undertaken an analysis of the oil data from sensing element 220, the data is displayed in an informative format for the user of system 200.

For example, overall oil quality may be reflected by one of a series of light emitting diodes (LEDs) 710 in the monitoring device 210. Various levels of oil quality may be reflected although the present embodiment reflects levels of <good>, <ok>, <fair>, and <change>. The latter setting—<change>— indicates the poor quality of the oil under analysis and the need for a change of the same.

A similar LED may be utilized to reflect the presence of excess and unwanted soot in the oil under analysis (LED 720) as well as excess and unwanted water (LED 730). These indicators, too, may further or individually reflect the need to replace motor oil before damage to the engine environment ensues. An overall system status LED 740 indicates that the monitoring device 210 and related equipment is in overall working order and that 'false positives' reflecting inaccurate oil readings are not being generated.

In another embodiment of the present invention, the interface 700 of the monitoring device 210 may reflect a variety of graphical outputs. For example, oil quality may be reflected by an LED or digital image output bar that rises or falls based on the oil quality. Oil quality may also be reflected by a digital output reflecting a number indicative of oil quality such that increased quality accuracy is possible.

Data generated as a result of various oil measurements reflects the overall quality of the oil. For example, normal oil capacitance and normal oil conductivity in conjunction with no water absorption is generally an indicator of overall good oil quality. To the contrary, high oil capacitance, low oil conductivity in conjunction with no water absorption may indicate worn oil quality. Low capacitance and low conductivity of the oil may be reflective of additive depletion. Soot contamination and water contamination may be reflected by rapid increases in oil capacitance notwithstanding normal oil conductivity in conjunction with a lack of water absorption and the presence of water absorption, respectively.

Various differential measurement outputs (or specific measurements or ranges of measurement) may be correlated to the aforementioned interface outputs (i.e., good v. change; graphical bars; numerical output). In some embodiments, this information may also or, alternatively, be reflected at the external computing device 250.

In some embodiments of the present invention, a series or array of oil sensors 220 may be utilized. The collective measurement data is analyzed by a signal monitoring device 210 or may be collected by individual monitoring device 210 and subsequently conveyed to the external computing device 250. Through collection and analysis of oil quality data from a series or array of oil sensors 220, an even more accurate oil quality reading may be obtained in that irregular and/or inaccurate oil readings (e.g., spikes in data) may be identified and filtered out of the final oil quality analysis. The collective measurement data may be, for example, batched and collectively analyzed or serially analyzed as data becomes available. Parallel analysis of portions of the oil measurement data may also take place.

While the present invention has been described in connection with a series of exemplary embodiments, these descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art.

The aforementioned differential measurement techniques may also be used for measuring fuel contamination. Using two sensor chambers—one that is sensitive to fuel contamination and one that is not sensitive to fuel contamination—and taking the differential signal between the two allows the for the detection of fuel contamination in oil. This technique is not limited to the above examples but can also be used to measure specific additives, contaminates or differences in other types of base stocks. Further, the technique is not limited to measuring electrical properties. The technique may be used to measure a change in size of a polymeric matrix due to a change in polarity of the oil, change in chemical composition of the oil due to degradation or change in size of the matrix due to contamination.

Differential inputs may include beads prepared where one type of bead can have its ionic group influenced by metals whereas another group will not be influenced in such a manner. Alternatively, one group of beads may be prepared such that they react differently than another group of beads in the presence of fuel. Differential measurement combinations may take into account one or more of different bead types, bead cross-linking, bead size, and bead preparation; the ability to change the physical properties of the sensor chambers (e.g., filters, electrode size, electrode shape, and so forth); and electrical excitation possibilities.

Various embodiments of the present invention may be implemented to analyze a variety of oil types and viscosities. The present invention may be implemented to analyze fluid substances at a variety of temperatures. The present invention may further allow for retrofitting of older oil pans or combustion engines while further allowing for design-specific configurations. In some embodiments of the present invention, a sensing element may be dedicated to a particular oil quality determination and used in tandem with a series of other sensing elements with respect to differential measurement of that particular quality or as part of an array with respect to a determining a variety of qualities utilizing various differential techniques. The present invention may be implemented in a variety of different operating environments including but not limited to gasoline engines, diesel engines, transmissions, turbines, transformers, gear boxes, vacuum pumps and other oil-reliant machinery.

Some embodiments of the present invention may employ various means of metal detection. For example, metal detection may be electrical; attaching a specific ion to a polystyrene bead may allow for a specific metal or group of metals to be detected. In one such example, one chamber of a sensor may contain beads with a hydrogen ion while the other chamber may contain beads with a barium ion. The sensor may be placed in an oil solution that contains lead whereby the lead would displace the hydrogen ion and electrically 'cap' the bead so that it does not change conductivity when polarity changes. The barium, on the other hand, would not be affected by the lead and will change conductivity only when the oil polarity changes. Taking the electrical differential of the signals generated by the beads in the two chambers will provide an indication of the lead contamination.

Metal detection may also be visible. For example, in the presence of copper, a calorimetric change takes place when the hydrogen ion is replaced by a copper ion. While the copper will replace the hydrogen ion, the barium ion will not be replaced. Measuring the differential of the visible spectra of the two chambers may provide an indication of, in this example, copper contamination in the oil.

Detection may also occur mechanically or electro-mechanically. The bead size may change by, for example, 5% when different ions are attached. Using a mechanical differential measurement methodology may provide an indication of specific metals. A spring or fulcrum may be used in some embodiments to show this differential.

While this invention has been described in conjunction with the specific exemplary embodiments outlined above, many alternatives, modifications, and variations may be apparent to those skilled in the art. Accordingly, the exemplary embodiments of the invention as set forth both are intended to be illustrative and not limiting except as otherwise set forth in the claims.

What is claimed is:

1. An oil quality monitoring system, comprising:
    a sensing element that generates oil measurement data associated with oil quality of a monitored oil sample, the sensing element comprising:
        a housing, and
        a plurality of chambers within the housing, the plurality of chambers including a first chamber and a second chamber, the first chamber including a first bead that responds to a first property of the monitored oil sample, the second chamber including a second bead that responds to a second property of the monitored oil sample; and
    a monitoring device coupled to the sensing element, the monitoring device comprising an application specific integrated circuit that differentially analyzes the oil measurement data from the plurality of chambers, and wherein the oil monitoring device displays an indicia of oil quality of the monitored oil sample in a user interface based on the differential analysis of the oil measurement data, the differential analysis including comparing a difference between oil measurement data from the first and second chambers.

2. The oil quality monitoring system of claim 1, wherein the first bead includes an ionically charged group.

3. The oil quality monitoring system of claim 1, wherein the first bead responds to a concentration of water, a concentration of soot, a pH, or a concentration of an additive package in the monitored oil sample.

4. The oil quality monitoring system of claim 1, wherein the plurality of chambers includes a third chamber containing a third bead, and the differential analysis includes comparing a difference between oil measurement data from two of the first, second, or third chambers.

5. The oil quality monitoring system of claim 1, wherein the first property is associated with any of a concentration of water, a concentration of soot, a pH, or a concentration of an additive package in the monitored oil sample, and the second property is associated with any other of the concentration of water, concentration of soot, pH, or concentration of the additive package in the monitored oil sample.

6. The oil quality monitoring system of claim 1, wherein the first chamber includes only the first bead, and the second chamber includes a plurality of beads.

7. The oil quality monitoring system of claim 1, wherein the oil measurement data include conductivities within at least two chambers of the plurality of chambers.

8. The oil quality monitoring system of claim 1, further comprising a thermistor coupled to the monitoring device, the thermistor disposed to measure oil temperature.

9. The oil quality monitoring system of claim 1, wherein at least one chamber from the plurality of chambers is covered by a filter that prevents suspended particles from passing into the covered chamber.

10. An oil quality monitoring system, comprising:
an array of sensing elements that generate oil measurement data
associated with oil quality of a monitored oil sample, each of the sensing
elements in the array of sensing elements comprising:
a housing, and
a plurality of chambers within the housing; and
a monitoring device coupled to the array of sensing elements, the monitoring device comprising a software module stored in memory and executable by a processor to differentially analyze the oil measurement data generated by the array of sensing elements and wherein the oil monitoring device displays an indicia of oil quality of the monitored oil sample in a user interface based on the differential analysis of the oil measurement data.

11. The oil quality monitoring system of claim 10, wherein the oil measurement data is batched and collectively analyzed by the monitoring device.

12. The oil quality monitoring system of claim 10, wherein the oil measurement data is serially analyzed by the monitoring device.

13. The oil quality monitoring system of claim 10, wherein portions of the oil measurement data are analyzed in parallel by the monitoring device.

14. The oil quality monitoring system of claim 10, wherein the oil measurement data are from at least two chambers of the plurality of chambers in each of at least two sensing elements in the array of sensing elements.

* * * * *